United States Patent
Paravastu et al.

(10) Patent No.: US 11,322,244 B2
(45) Date of Patent: May 3, 2022

(54) SYSTEM AND METHOD FOR DETERMINING ANISOMELIA CONDITION OF A SUBJECT USING IMAGE ANALYSIS AND DEEP NEURAL NETWORK LEARNING

(71) Applicants: Seshadri Paravastu, San Jose, CA (US); Radha Samavedam Paravastu, San Jose, CA (US)

(72) Inventors: Seshadri Paravastu, San Jose, CA (US); Radha Samavedam Paravastu, San Jose, CA (US)

(*) Notice: Subject to any disclaimer, the term of this patent is extended or adjusted under 35 U.S.C. 154(b) by 0 days.

(21) Appl. No.: 17/203,499

(22) Filed: Mar. 16, 2021

(65) Prior Publication Data
US 2021/0233643 A1 Jul. 29, 2021

(51) Int. Cl.
*G16H 30/20* (2018.01)
*G06N 3/08* (2006.01)
(Continued)

(52) U.S. Cl.
CPC .......... *G16H 30/20* (2018.01); *A61B 5/0077* (2013.01); *A61B 5/1072* (2013.01);
(Continued)

(58) Field of Classification Search
CPC .... G16H 30/20; A61B 5/0077; A61B 6/5247; A61B 5/1072; A61B 6/50; A61B 5/7267;
(Continued)

(56) References Cited

U.S. PATENT DOCUMENTS

| | | | |
|---|---|---|---|
| 5,823,974 A | * | 10/1998 | Grassi .................. A61B 5/1072 600/595 |
| 10,555,689 B1 | * | 2/2020 | Marquez .............. A61B 5/7267 |

(Continued)

OTHER PUBLICATIONS

Barton "An application of neural networks for distinguishing gait patterns on the basis of hip-knee joint angle diagrams", Gait & Posture 5 (1997) 28-33 (Year: 1997).*

(Continued)

*Primary Examiner* — Oommen Jacob

(57) ABSTRACT

The present invention is an Deep Neural Network based technology relating to diagnosis of Anisomelia, also referred to as Leg Length Discrepancy (LLD). This invention is a system and method, which comprises of a diagnosis device referred to as the "LEG-Minder" device that is typically installed in a diagnosis center setting, and diagnoses for LLD on the basis of a neural network model with patient's leg photos or x-rays thereof; and a neural network learning server referred to as the "LEGislator" which is connected to the Internet and performs Deep Neural Network (DNN) learning, on the individual LLD databases generated by a plurality of the "LEG-Minder" device(s). In particular, the present invention relates to a technology in which patient's leg photos (or x-rays) and the corresponding diagnostic result data are acquired in each diagnosis center and then individually uploaded to the LEGislator; and then, on the basis of the uploaded information the LEGislator performs DNN learning to generate an upgraded neural network model, which is then disseminated to the "LEG-Minder" device(s), providing them the latest learnings, which subsequently helps in improving the diagnosis accuracy. This invention optimizes the diagnosis environment of the diagnosis center for Anisomelia.

20 Claims, 18 Drawing Sheets

Overall system and Claims

(51) Int. Cl.
*G06N 3/04* (2006.01)
*A61B 5/107* (2006.01)
*A61B 5/00* (2006.01)

(52) U.S. Cl.
CPC ............. *A61B 5/7267* (2013.01); *G06N 3/04* (2013.01); *G06N 3/08* (2013.01)

(58) Field of Classification Search
CPC ... A61B 5/1073; A61B 5/1074; A61B 5/1077; G06N 3/08; G06N 3/04; G06N 3/02–08; G06N 3/088
See application file for complete search history.

(56) References Cited

U.S. PATENT DOCUMENTS

| | | | | |
|---|---|---|---|---|
| 2018/0289334 | A1* | 10/2018 | De Brouwer | G06K 9/00288 |
| 2019/0133693 | A1* | 5/2019 | Mahfouz | A61B 6/5229 |
| 2019/0213388 | A1* | 7/2019 | Makeev | A61B 5/015 |
| 2020/0129237 | A1* | 4/2020 | Ay | G16H 50/20 |
| 2020/0215324 | A1* | 7/2020 | Mantovani | A61B 5/0022 |
| 2020/0321074 | A1* | 10/2020 | Tran | G16B 20/20 |
| 2021/0233643 | A1* | 7/2021 | Paravastu | A61B 5/1072 |
| 2021/0335028 | A1* | 10/2021 | Yang | G06T 15/20 |

OTHER PUBLICATIONS

Zheng "Deep Learning Measurement of Leg Length Discrepancy in Children Based on Radiographs", Radiology 2020; 296:152-158 (Year: 2020).*

Tsai "Anatomical landmark localization via convolutional neural networks for limb-length discrepancy measurements", Pediatric Radiology (2021) 51:1431-1447 (Year: 2021).*

* cited by examiner

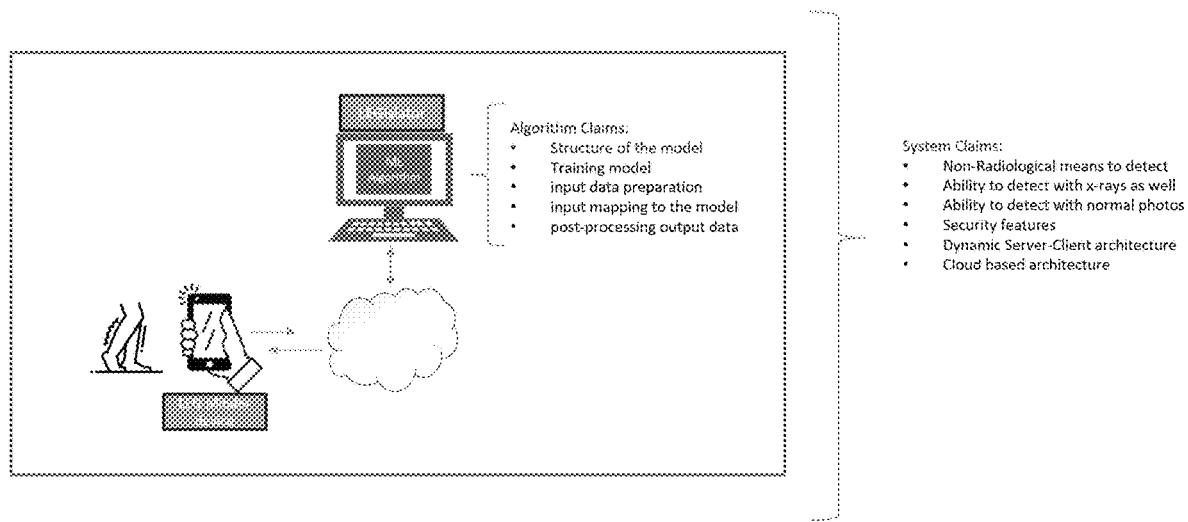
Figure 1 Overall system and Claims

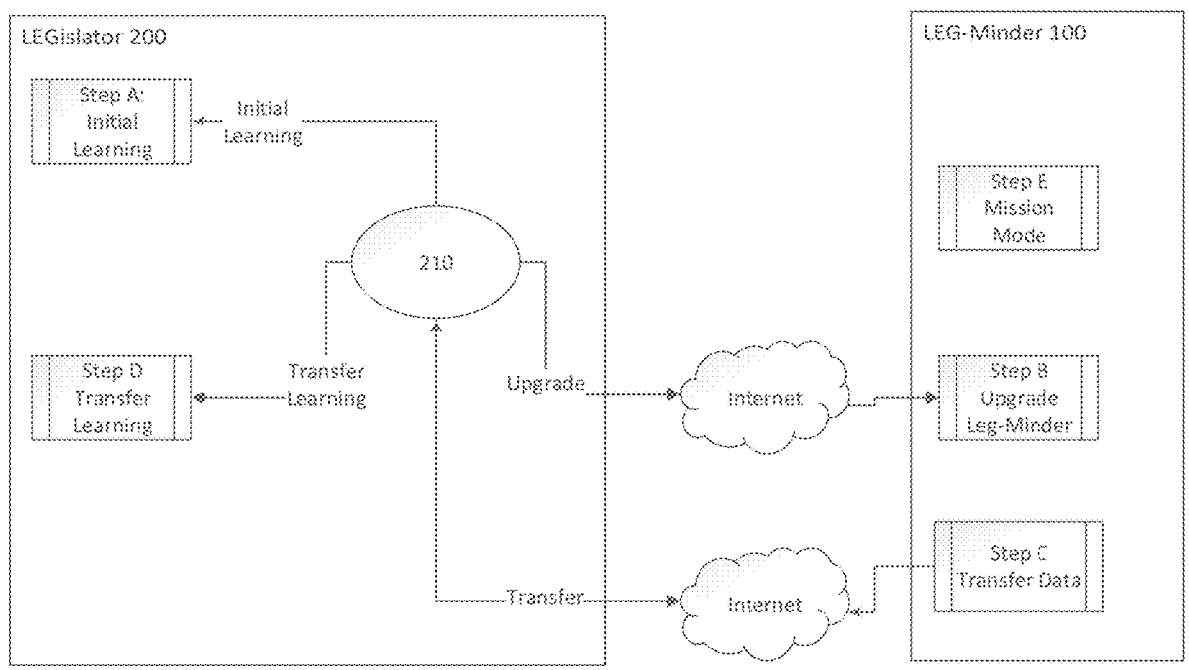
Figure 2 System Level Architecture

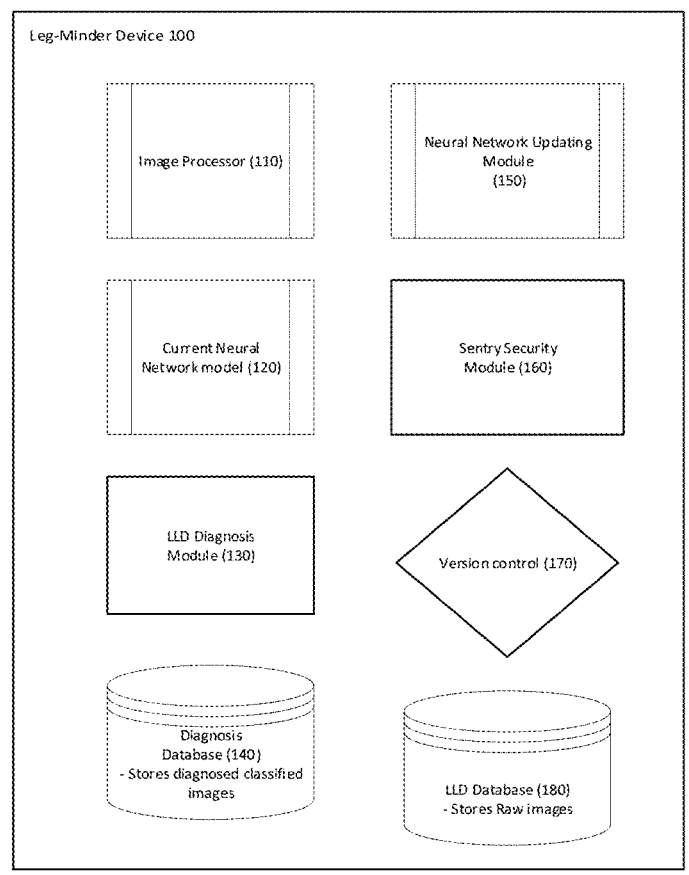
Figure 3 Component Level architecture – LEG-Minder Device

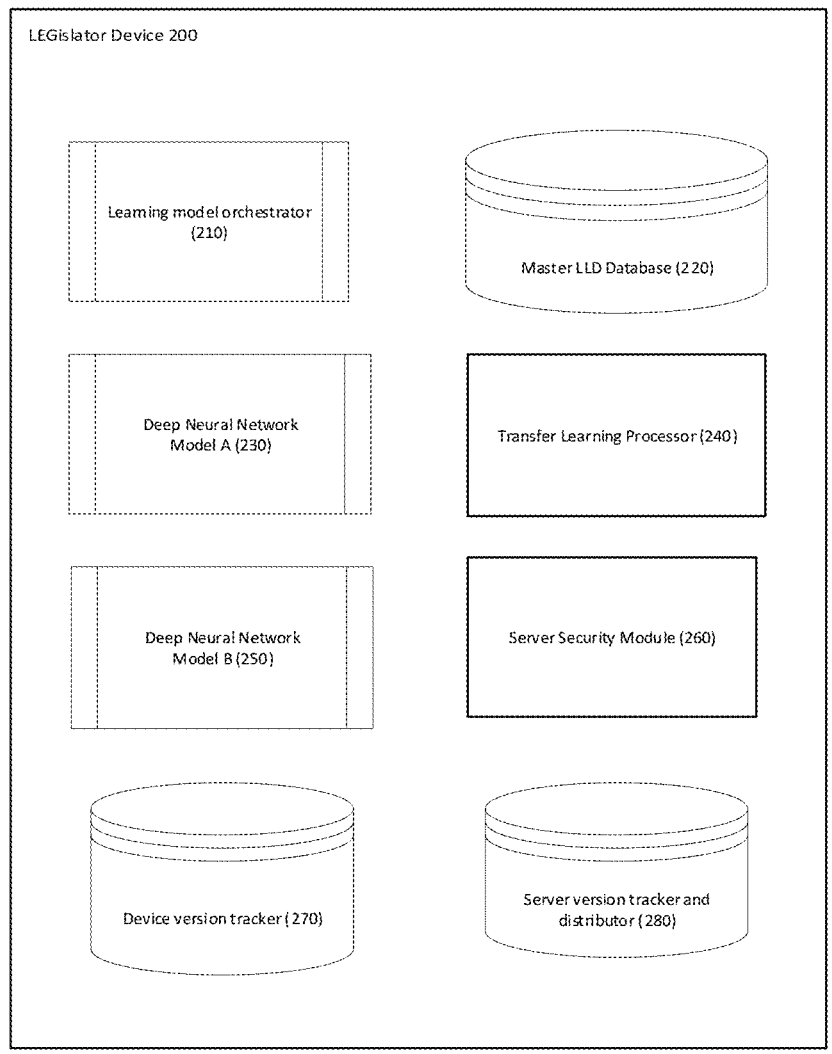
Figure 4 LEGislator - Master Neural Network Server

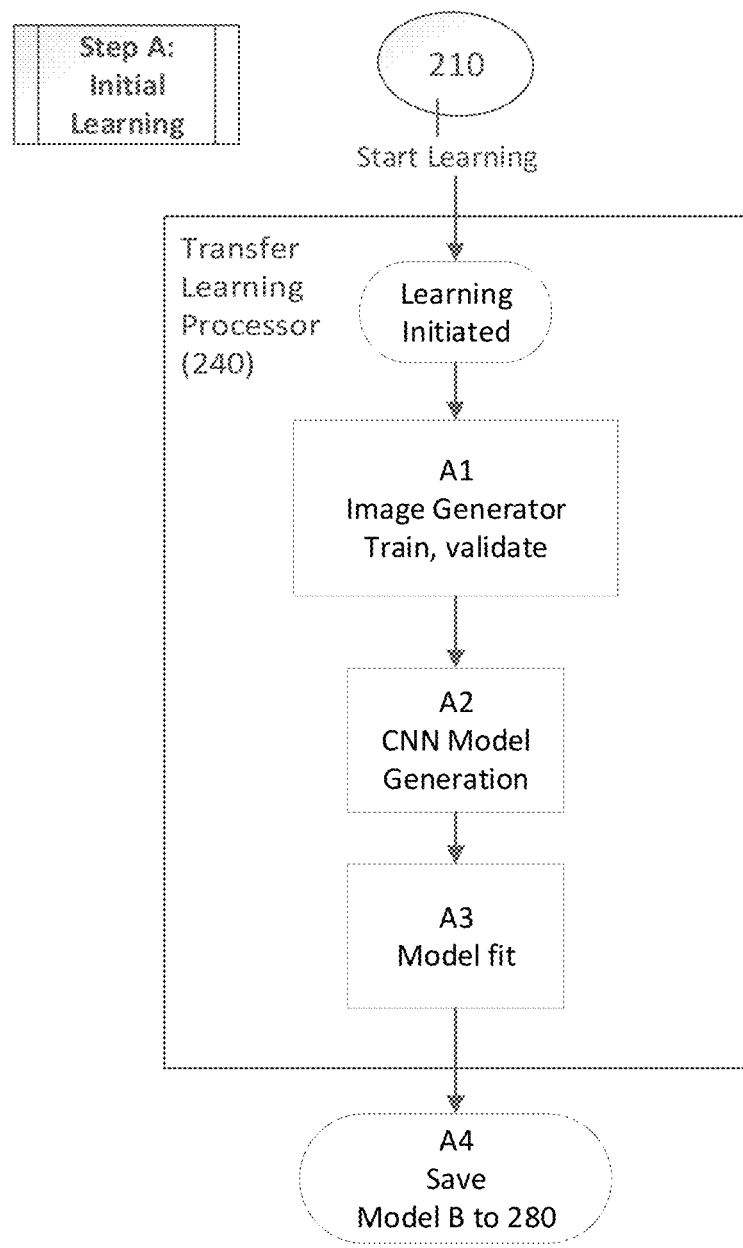
Figure 5 Step A – Initial Learning

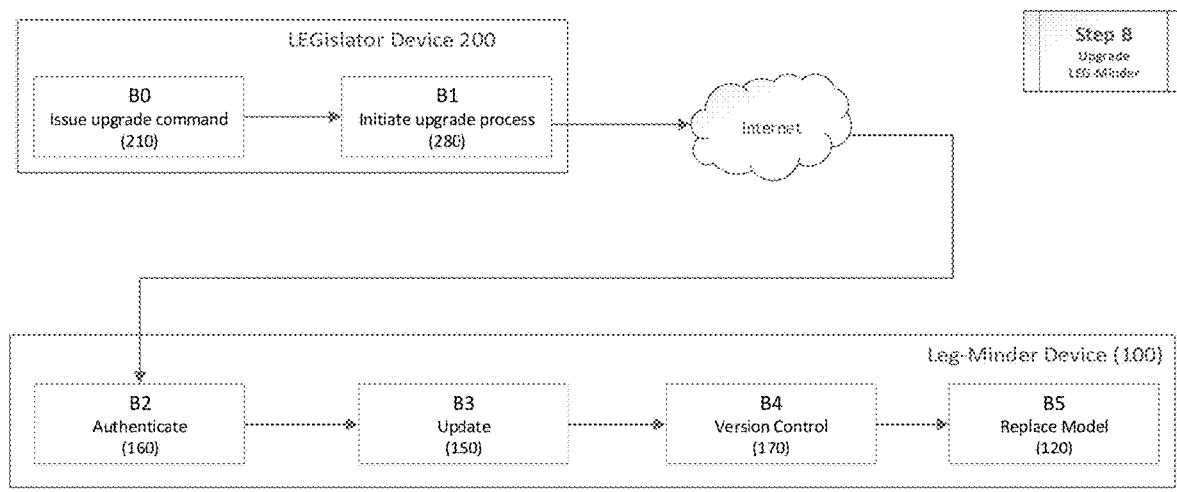
Figure 6 Step 8 Upgrade LEG-Minder

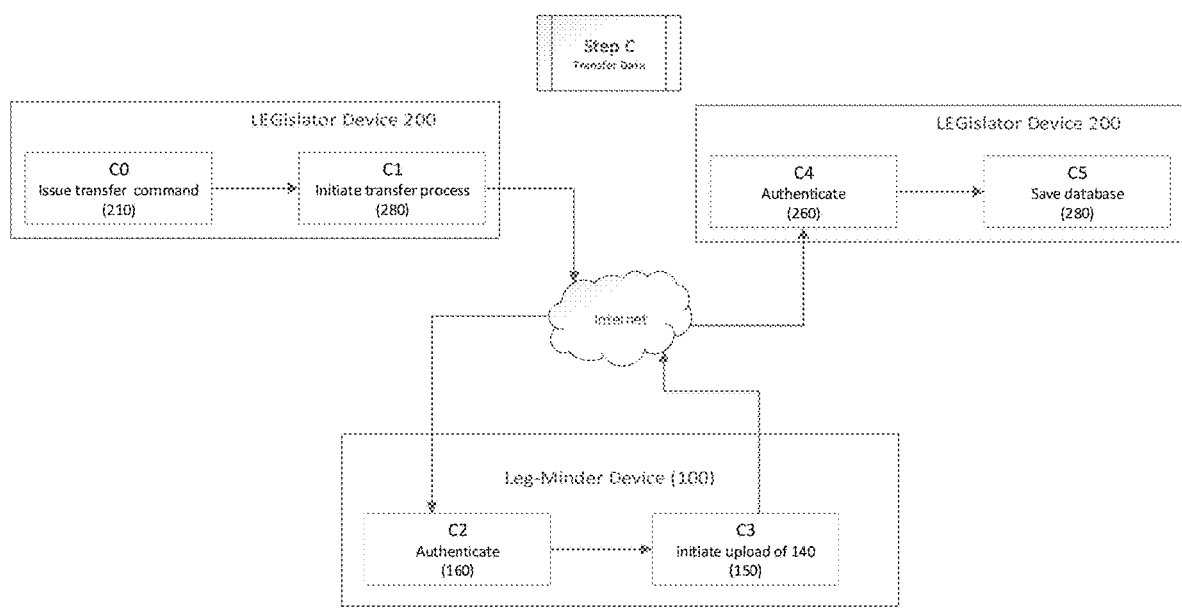
Figure 7 Step C: Transfer Data

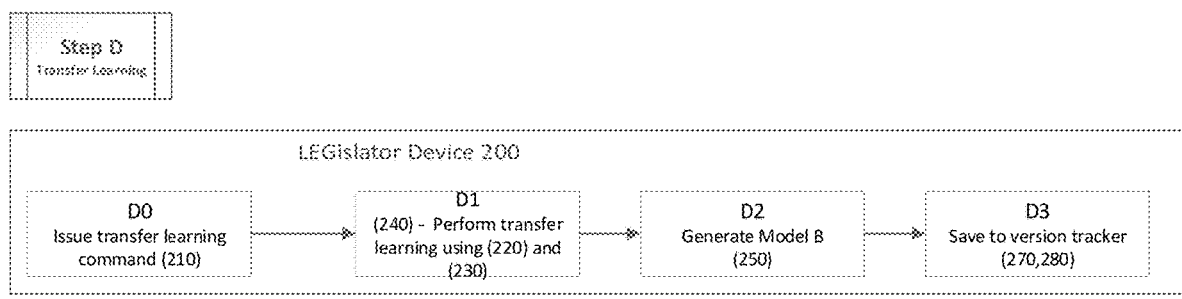
Figure 8 Step D Transfer Learning

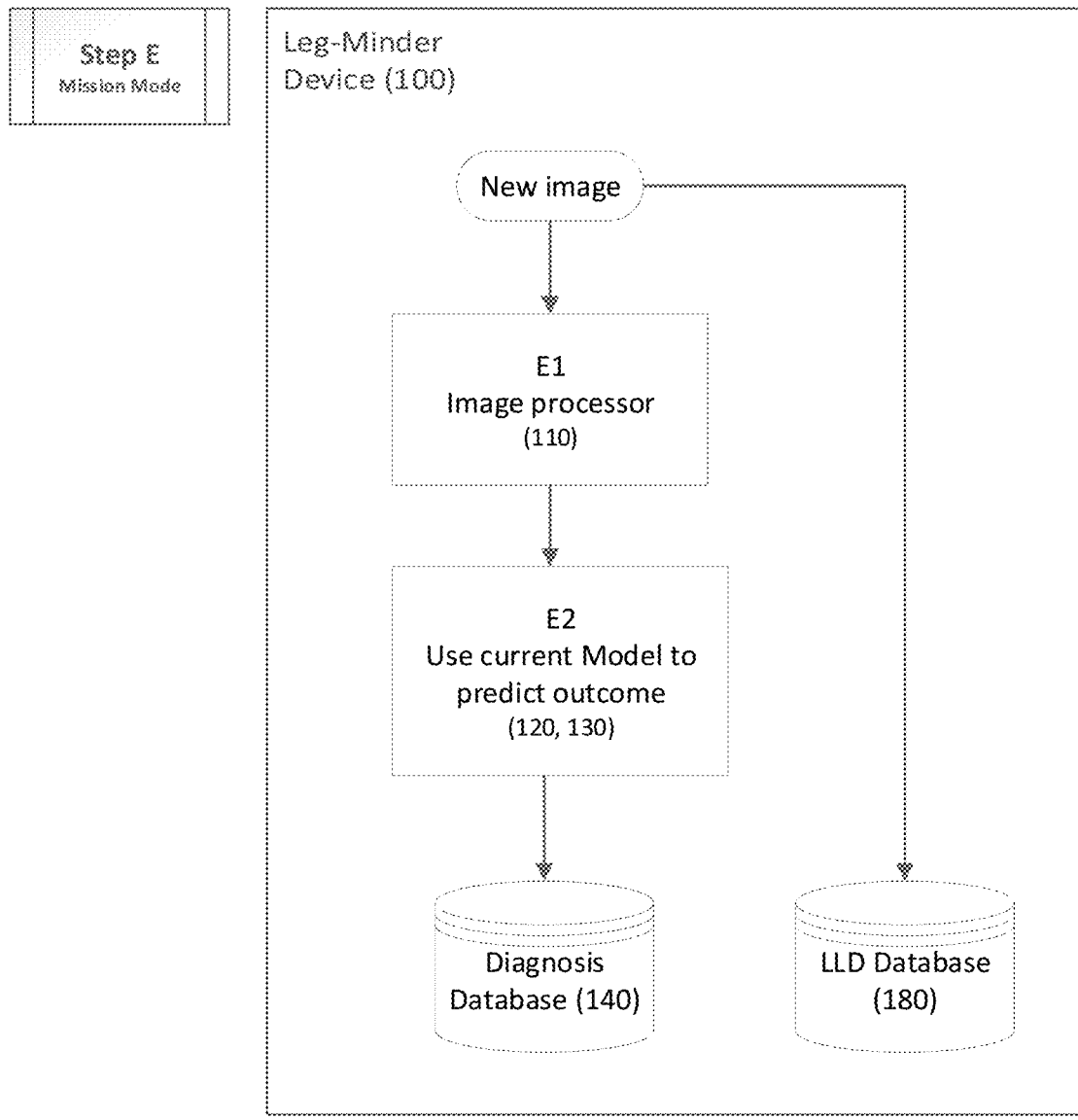
Figure 9 Step E Mission Mode

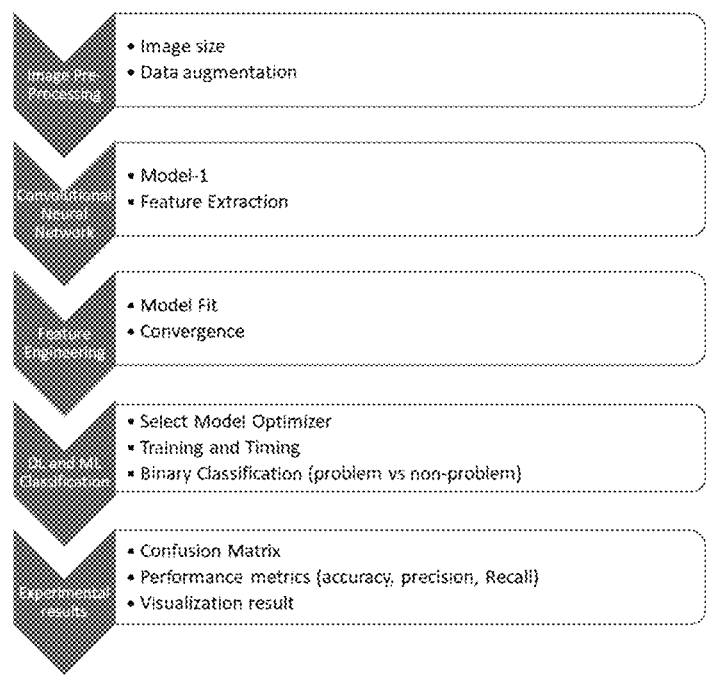
Figure 10 Pipeline Architecture for Neural Network Model Generation

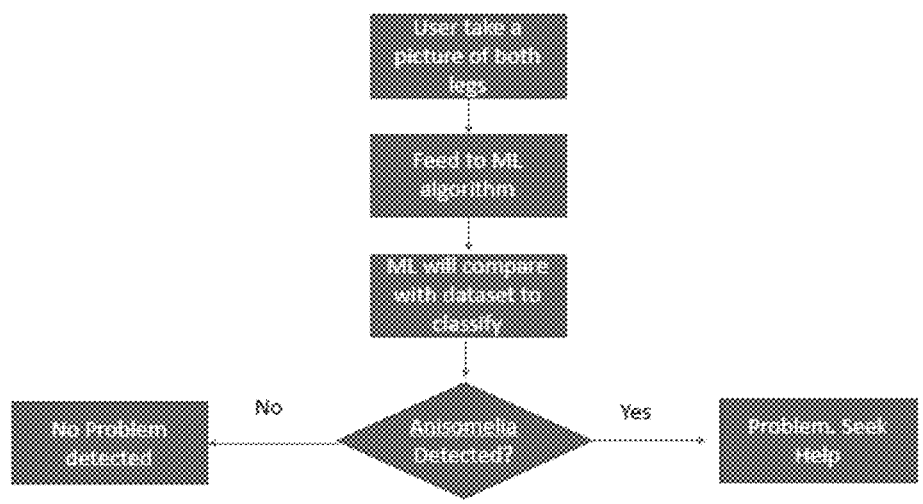
Figure 11 Proposed user flow with the LEG-Minder device

```
Model: "sequential"
_____
Layer (type)                 Output Shape              Param #
=================================================================
conv2d (Conv2D)              (None, 298, 298, 16)      448
_____
max_pooling2d (MaxPooling2D) (None, 149, 149, 16)      0
_____
conv2d_1 (Conv2D)            (None, 147, 147, 32)      4640
_____
max_pooling2d_1 (MaxPooling2 (None, 73, 73, 32)        0
_____
conv2d_2 (Conv2D)            (None, 71, 71, 64)        18496
_____
max_pooling2d_2 (MaxPooling2 (None, 35, 35, 64)        0
_____
flatten (Flatten)            (None, 78400)             0
_____
dense (Dense)                (None, 512)               40141312
_____
dense_1 (Dense)              (None, 1)                 513
=================================================================
Total params: 40,165,409
Trainable params: 40,165,409
Non-trainable params: 0
_____
```

*Figure 12 Convolution and Pooling*

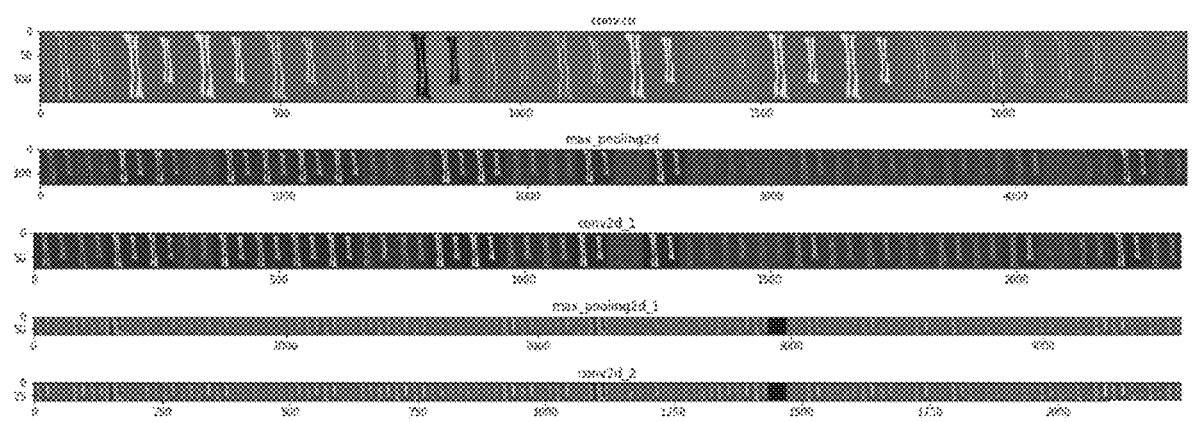
Figure 13 Convolution layers and Max Pooling

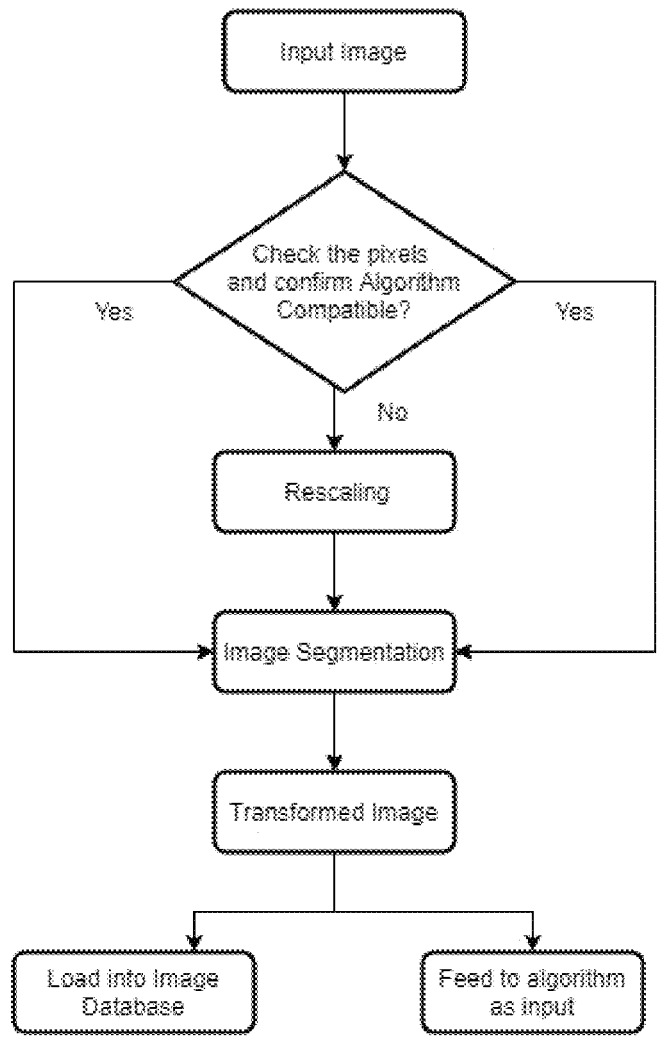
Figure 14 Image Pre-Processing Flowchart

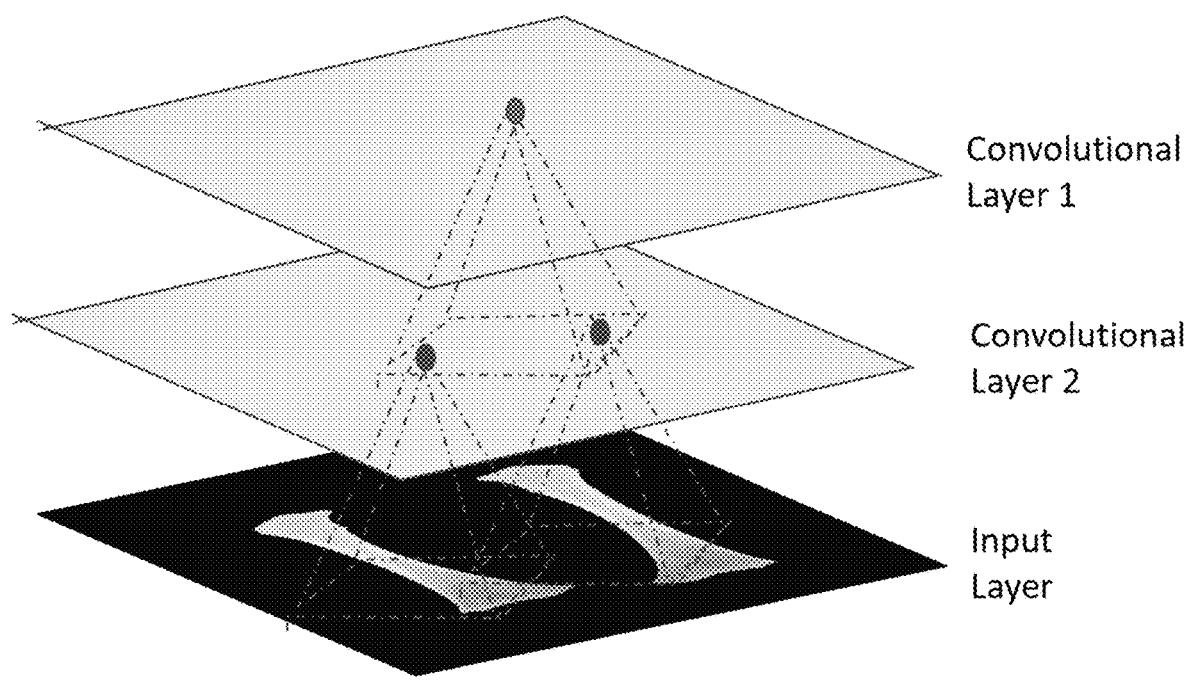
Figure 15 Convolution Building

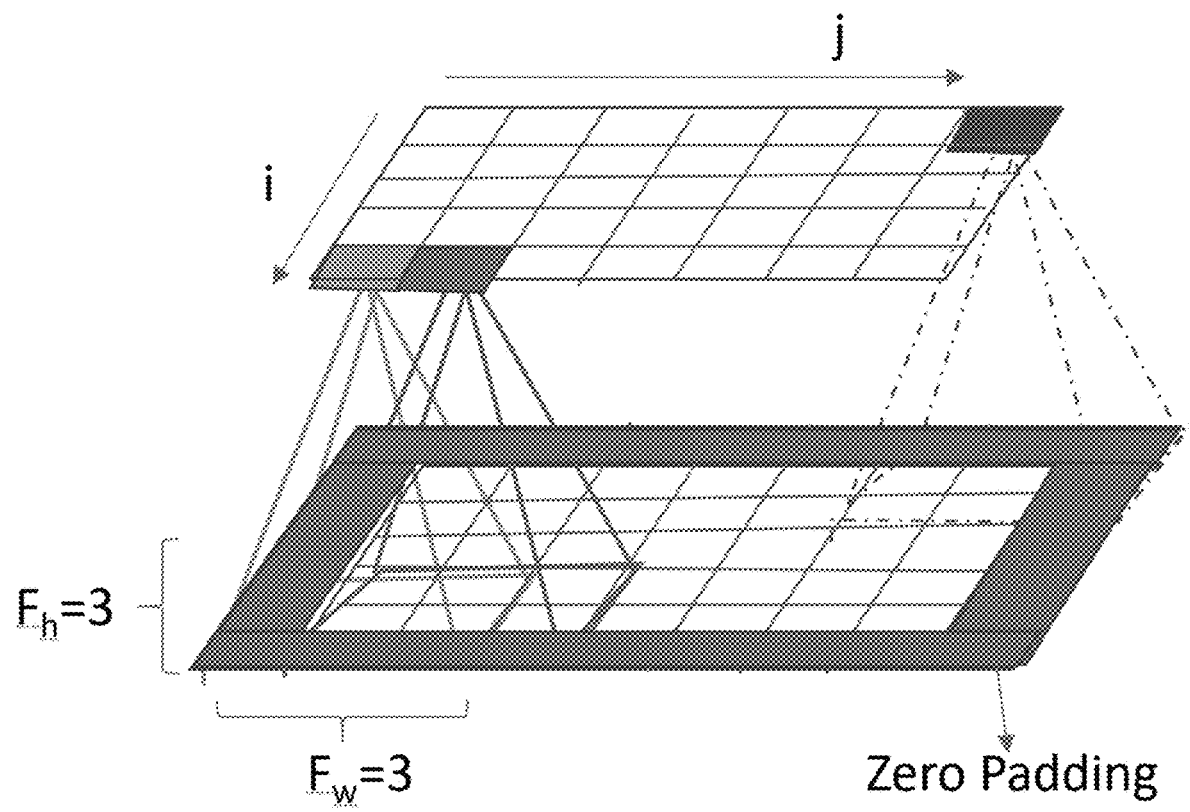
Figure 16 Padding Implementation

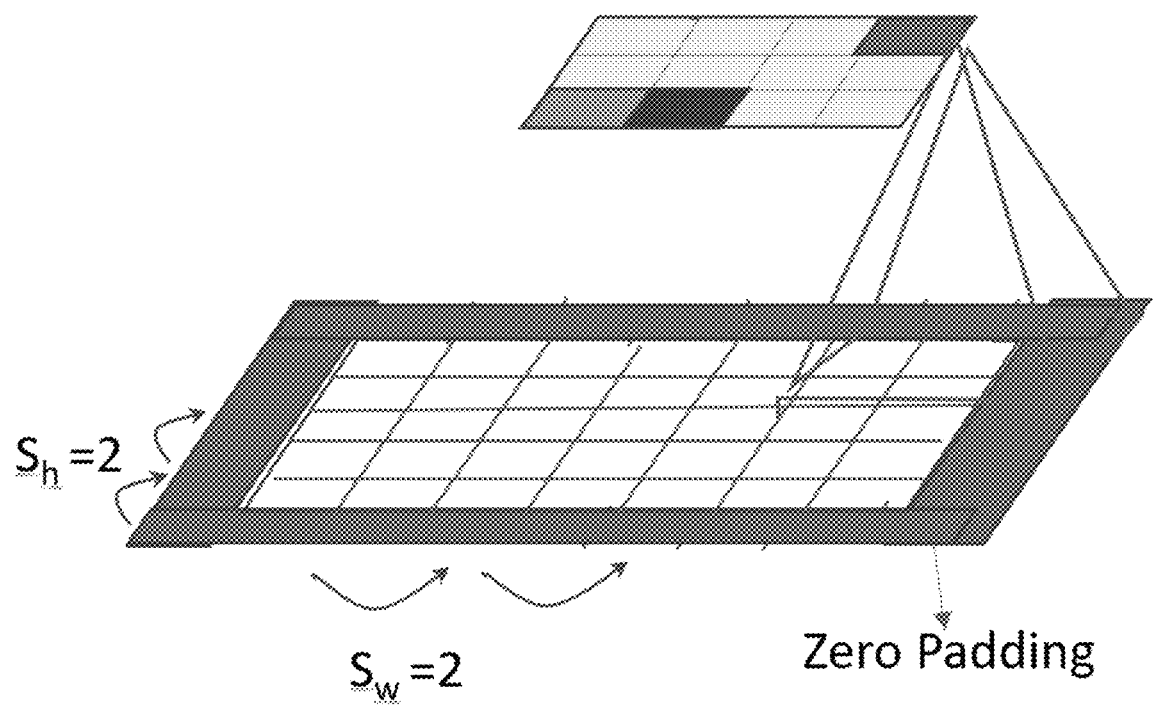
Figure 17 Dimensionality Reduction

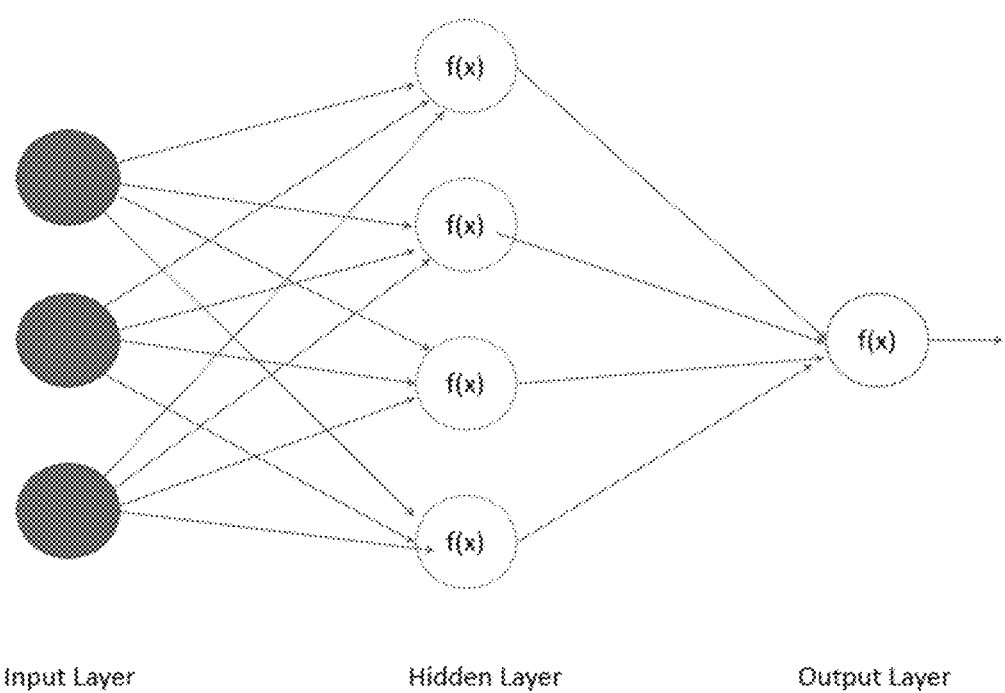
Figure 18 Deep Neural Network

SYSTEM AND METHOD FOR DETERMINING ANISOMELIA CONDITION OF A SUBJECT USING IMAGE ANALYSIS AND DEEP NEURAL NETWORK LEARNING

FIELD OF INVENTION

Anisomelia or Leg length discrepancy (LLD) is a widespread and common condition involving abnormal loading of the lower extremity and lumbar joints. While simple X-rays can resolve between 70% and 80% of diagnostic problems, only one-third of the world's population has diagnostic imaging access. This proposed solution elegantly strengthens the processes for the assessment, adoption, and use of appropriate health technologies for diagnostic imaging with simple digital photographs (e.g., from a smartphone) and avoids the expensive need for X-ray equipment or can become a substitute for cases that need radiation protection of the public, workers, patients, and the environment.

Anatomic leg-length inequality is near-universal—Leg length discrepancy (LLD) affects up to 90% of the general population with a mean discrepancy of 5.2 mm. In most such cases, LLD is mild (<20 mm). When overlooked during early medical examinations, spinal severe cord misalignment and kyphosis occur in children born with this condition. So, early detection is vital in Anisomelia. This system addresses aiding in early-detection for every human being. While simple X-rays can resolve about 75% of diagnostic problems, nearly half of the world's population has no diagnostic imaging access per World Health Organization). Inexpensive non-radiology equipment to perform a simple test to detect LLD is very much needed. Hence the need for the system that can detect this. Most valuable features for new inspection method like the proposed system here will be:
  a. No radiation exposure
  b. Equal or more accurate than current inspection methods
  c. Is cheaper The present invention is a technology relating to a Leg Length Discrepancy diagnosis system using Deep Neural Network (DNN) learning, which comprises of a diagnosis "Leg-Minder" device that is installed in each diagnosis center and determines the patients legs to either have a height discrepancy or not on the basis of a neural network model with a patient leg photograph or a potential radiographic image (eg X-ray image) as inputs; and a neural network learning server "LEGislator" that is connected to the internet and performs DNN Learning on the LLD database of a plurality of "LEG-Minder" devices in the network.

In particular, the present invention relates to a technology in which patient's leg photos and diagnostic result data are acquired in each diagnosis center and then uploaded to the neural network learning server "LEGislator device". Then on the basis of this information the learning server performs DNN learning on its neural network model so as to generate an upgraded neural network model. This upgraded model is later downloaded to all the LEG-Minder devices in the network. By the above constitution, the LEG-Minder device becomes a part of a neural network model, which is optimized to the diagnosis environment within a diagnosis center.

BACKGROUND ART

Anisomelia is classified as either anatomical (structural) or functional. Structural is side-to-side differences in lower limb length, while functional is due to bio-mechanical abnormalities of joint function in the lower limbs (athletes). The causes for LLD can be Congenital or can be acquired. Congenital causes include phocomelia and dysgenetic syndromes. Acquired causes include: dysplasias, Ollier's disease, polio & osteomyelitis, neurofibromatosis; septic arthritis; fractures; and also surgically induced. LLD can exist from childhood or it can develop in adult life. The clinical methods (direct and indirect methods) in common use to measure leg length discrepancy (LLD) cannot always meet the demands of precision and accuracy based on numerous studies. Some of the current clinical methods of assessing this discrepancy include tape measures, planks and blocks to level the pelvis, and x-rays including scanograms and ultrasounds. Studies have shown clinical assessments of the examiners were incorrect by greater than 5 mm in 29% of subjects.

In addition, it also turns out that these methods are:
Expensive (both time-wise and $-wise)
Not necessarily prescribed to every patient due to exposure to radiation of the pelvic region.

The diagnosis alone can be complicated. In simple words, it involves:
1) The attending physician needs to clearly observe the patients posture and suspect LLD condition
2) The physician should have the presence of mind to initiate the radiological process for the patient
3) The clinician reading the x-rays has to accurately classify this to be a potential LLD problem and
4) The patient has to follow through the long process and stick with it to complete the process.

LLD diagnosis and detection is not a part of regular annual medical check-ups for anyone and especially so for younger children in the age group 5-12. When LLD is not identified and fixed early, posture deformation, gait asymmetry, and lower-joint damages can occur in later years. Apparent LLD condition is more common than true LLD, some of the symptoms for which include:
  a. Scoliosis
  b. Flatfeet
  c. Unleveled hips In cases where the apparent LLD cannot be confirmed via X-rays, this proposed system and method is an indispensable method for accurate diagnosis.

Some biases are prevalent and endemic in medicine. Such biases could result in deeply fallible and flawed medical diagnoses/data. This flawed data and decisions can amplify harm caused to the complex human body system. Since the initial screen is done under the experience and skill by a practitioner, the accuracy of the first examination, which sometimes may be affected by screeners' personal condition, is the trigger for the course of action a patient/physician takes. Therefore, its important for this to be accurate and to 'de-bias' via qualitative and quantitative means.

As discussed above, the analysis and classification of LLD can be complex and sometimes overlooked even for a trained eye. This gap is addressed by using Machine Learning (ML). ML can be used to perform computationally complex tasks leading to determination of certain conditions in high-risk patients. This invention uses ML technologies to diagnose LLD. The computational means provides consistent and reliable first diagnosis results without relying solely on the skills of the screeners and the associated problems as discussed in the above paragraph. This makes the invention an elegant and easier solution to diagnose LLD with improved/speedier diagnosis creating an economical long-term solution to diagnose the LLD condition.

Further, in the current art, individual diagnosis centers are introducing various technologies in their own tests yet, which renders diagnosis technology inconsistent and insufficiently reliable. Because each of large diagnosis centers individually utilizes diagnostic result data of their own, process can be quite complex. An electronic means to provide uniformity to the solution removes complexities arising from various biases. Often Artificial Intelligence (AI) is used for these processes as increasingly complex diagnosis can be automated to not miss the intricate details.

DISCLOSURE OF INVENTION

Technical Problem

The present invention is proposed with reference to the above-mentioned problems in the Background Art. The objective of the present invention is to provide an elegant, speedy, and accurate LLD diagnosis system and method, using computational approaches such as Deep Neural Network (DNN) learning, in which diagnosis accuracy of devices can be be gradually improved. This is performed by a client-server type architecture with an Internet-connection without individually modifying each of neural network models. This invention uses Deep Neural Learning Network by which computers may think and learn like a human constantly and categorize objects and hence is Artificially Intelligent.

Technical Solution/Algorithm

Image classification techniques are used by computer vision tasks (e.g., segmentation, object detection, and image classification) and pattern recognition exploiting handcrafted features from a large-scale database, thus allowing new predictions from existing data.

In the ML algorithm associated with this invention, images are parsed into multiple layers and computationally higher-level features are extracted from the raw input images. Progressively, algorithm is trained on pre-classified images and is the validated on a separate set of pre-classified images. From the predictions on the training images, ML algorithm compares the expected result and charts an auto correction sequence. The ML algorithm thus learns from existing data and derives a model which is then used to predict new images presented to it.

Mathematically, the ML algorithm uses Convolutional Neural Network (CNN) transforms, which apply functions such as convolution, kernel initialization, pooling, activation, padding, batch normalization, and stride to the images for processing. The CNN then adaptively learns various image features, and performs an image transformation, focusing just on the features that are highly predictive for a specific learning objective. Leveraging such patterns, classifiers like sigmoid and Softmax classifiers are then applied to learn the extracted and important features. This results in a Neural network model that can be used to make predictions on test or patient leg images.

The current method involves using pipelines for LLD classification using ML techniques to develop a lightweight CNN model for automatic detection of LLD in various bilateral leg pictures or bilateral leg x-rays. This lightweight model is then adopted into the LEG-Minder devices.

The ML models were trained using several simulated LLD image dataset with different parameters and filters in the LEGislator. With every iteration, hyperparameters are fine-tuned, activation functions are optimized to improve the accuracy of the model. Then, binary classification is employed for detection. This model is deployed in the LEG-Minder devices. Periodically, the LEG-Minder database is uploaded to the LEGislator which then performs an upgrade on its neural network model version. Then the upgraded model is deployed again into the LEG-Minder devices. From a LEG-Minder device standpoint, the end user can simply upload a normal photograph of the legs or a radiograph or a photograph in a bilateral fashion and feed it to the ML algorithm, which then compares and classifies the image for LLD detection. This is summarized in the proposed user-flow as shown in FIG. 11.

Advantages

The framework proposed here is practical and can be easily compared to handcrafted measurements by practitioners. The potential outcomes of this invention can be applied to expand into other areas of ML based classifications in the medical field as well as specifically also measure the discrepancy more accurately. The work can also be extended to predict results on plain photographs (non-xray). For example, in a group of legs—as in a class picture type of setting in a school) to quickly identify potential issues and alert the parents to seek further medical help and aid in early detection. The proposed solution is elegant enough to be applied in the context of reaching young children in underprivileged and underserved communities by identifying LLD early enough with a simple photograph which can be uploaded remotely into the LEG-Minder device with appropriate controls via a local medical practitioner as opposed to getting more expensive X-rays and qualified technicians to read them. This also helps prevent expensive deformities later in the life with a trigger to seek medical help for the necessary intervention early enough. The current system and method here offers a elegant, speedy, and accurate LLD diagnosis system using computational approaches:

- When compared to the existing clinical methods (direct and indirect methods) this computational method will be more precise, can take advantage of the continual learning to update the knowledge and is computationally more accurate than human estimation and measurements. Inaccurate diagnosis by a human doctor can lead to higher illness burden on patient and well as the hospital, and insurance companies. This innovation helps reduce the patient and hospital burden.
- The fact that this algorithm can even work with non-radiological images and can use normal photographs will enable the use of technology even for those patients that cannot tolerate exposure to radiation of the pelvic region.
- The use of normal photographs also allows the invention to be used in under-served and under privileged communities where radiography reach isn't available. This invention will spread the reach of the LLD diagnosis to nearly half the world's population that does not have yet access to radiological equipment.
- The global radiology gap is far less discussed than infectious-disease outbreaks and natural disasters, but its dangers to public health are every bit as urgent!! In certain countries, there is a serious deprivation of radiologists. The use of normal photographs will allow the population to use this technology that can provide more accurate diagnosis based on normal photographs and technicians can be trained to operate it vs more qualified radiologists.

Time taken from the point of first patient-doctor contact to the time diagnosis is completed can be significantly reduced with this invention. Since there is no scheduling to be made with radiology department, patient having to come back at another time for getting X-rays, once taken, waiting for the Radiologist to read the X-rays and then passing the information to the orthopedic doctor can all be cut down to a few minutes as the technician or the orthopedic doctor themselves can use the device to diagnose LLD problem in a matter of few minutes.

BRIEF DESCRIPTION OF DRAWINGS

FIG. 1 Overall system and Claims illustrates the overall system including LEG-Minder and LEGislator for Leg Length discrepancy diagnosis.

FIG. 2 System Level Architecture is a block diagram of the LEG-Minder and the LEGislator combination according to the present invention.

FIG. 3 Component Level architecture is a block diagram of the LEG-Minder device which forms the patient image portion of the invention.

FIG. 4 LEGislator Master Neural Network Server is a block diagram of the Learning server which forms the cloud-based algorithm updater portion of the invention.

FIG. 5 Step A Initial Learning depicts the steps involved with initial learning by LEGislator FIG. 6 Step B Upgrade LEG Minder depicts the process of upgrading the LEG_Minder by the LEGislator FIG. 7 Step C: Transfer Data depicts the steps involved with LEG-Minder transfer of data FIG. 8 Step D Transfer Learning depicts the steps involved with transfer learning by LEGislator FIG. 9 Step EMission Mode depicts the steps involved with operational mode of LE-Minder FIG. 10 Pipeline Architecture for Neural Network Model Generation is a block diagram of the Learning server's pipeline architecture.

FIG. 11 Proposed user flow with the LEG-Minder device is a flow chart of how the user would use the LEG-Minder device.

FIG. 12 Convolution and pooling shows the configurations and the summary of transformations.

FIG. 13 Convolutional layers and Max Pooling shows the traversal of an image though all the convolutional and the pooling layers.

FIG. 14 Image Pre-Processing Flowchart shows the first step in the algorithm which is pre-processing of input.

FIG. 15 Convolution Building shows the architecture of the convolutional neural network.

FIG. 16 Padding Implementation shows how padding is implemented in the algorithm.

FIG. 17 Dimensionality Reduction shows how performance improvements are implemented to achieve dimensionality reduction.

FIG. 18 Deep Neural Network shows the implementation of back propagation

ALGORITHM SUMMARY

1. As a first step, the algorithm pre-classifies generated images into a training set and a validation set.
2. Next, the algorithm addresses image normalization. Since the input raw data may not already be normalized, i.e., there is no control over what pixel size a user may input, the algorithm rescales the images to normalize all the input parameters. After this step all the images will have identical parameters although the content inside may be very different.
3. Then the algorithm pre-processes the image data. Image pre-processing is done by augmentation of the existing data and considers overfitting the data.
4. Then, the algorithm expands the scope of the input images to account for yet unseen image variations by amending the existing images to overfit while training the data, by use of various transforms like rotation, flipping, skewing, relative zoom, and other affine transformations such as translation, rotation, isotropic scaling and shear.
5. Next, the algorithm will set a specific batch size to process a batch of images at once.
6. Then, the algorithm will invoke a binary class mode because there are only two classes for classification—namely the LLD or non-existing LLD case.
7. Then the algorithm will pass the training image set via convolutions to learn particular features of the training images.
8. The algorithm then will initiate pooling and the image traversal through the above path of convolutions while extracting the next set of features.
9. The algorithm will then stack multiple sets of convolutions and pooling layers as described in the prior two steps. The size of the subject image is progressively reduced, which is then fed into the dense layers.
10. The algorithm also implements a softmax classifier to reduce binary loss through the above process steps.
11. Learning rate is then adjusted for convergence to arrive at a solution.
12. The algorithm will then output a single neuron with a sigmoid activation which gives the final result on the processed image.
13. Next, the algorithm will setup the same on a validation dataset to verify that the algorithm is classifying accurately.
14. The algorithm is now trained and can accept a new image upon which it will process the feature extraction identified earlier to finally arrive at a classification output on the single neuron.

Algorithm Details:

Image Pre-Processing (Step 3 in Algorithm):

Image preprocessing refers to step 3 defined in the algorithm summary. The system can accept various image formats, such as JPEG, GIF, PNG, etc., typically used for photographic images. Formats such as DICOM, NIFTI, and Analyze AVW are used in medical imaging. Formats such as TIFF, ICS, IMS, etc., are used in microscope imaging. Image data will be stored as a mathematical matrix.

Approximately, 2D image of size 1024-by-1024 is stored in a matrix of the same size. It takes an image as an input and recognizes image pixels and converts it into a mathematical matrix. As shown in FIG. 14, the algorithm then checks for the image's compatibility with predictive model. If the image is compatible, it is fed directly to the image segmentation section skipping the rescaling. During the rescaling operation, first, a combination of linear filters and non-linear filters are used to remove the undesirable properties in the input image. Image enhancement, if needed, is accomplished either in spatial or frequency domain as necessary. In the Image Segmentation section, the image is segmented to separate the background and foreground objects. All the objects are marked with different markers setting a clear path for the predictions using the ML model. The transformed image is then stored in the database and fed to a predictive model for further processing. The Image Preprocessing flowchart shows a detailed outline of the process.

Convolutional Neural Network Layers (Steps 7, 8, 9) in Algorithm:

Refer to FIG. 15, and steps 7, 8, 9 in the algorithm summary. In the convolutional neural network, the neurons in the first convolutional layer are not connected to every single pixel in the input image, but only to pixels in their receptive fields. In turn, each neuron in the second convolutional layer is connected only to neurons located within a small rectangle in the first layer. This architecture is selected so that it allows the network to concentrate on small low-level features in the first hidden layer, then assemble them into larger higher-level features in the next hidden layer, etc.

A neuron located in row i, column j of a given layer is connected to the outputs of the neurons in the previous layer located in rows i to i+$f_h$-1, columns j to j+$f_w$-1, where $f_h$ and $f_w$ are the height and width of the receptive field as shown in FIG. 16 padding implementation. Zero padding is implemented such that a layer has the same height and width as the previous layer by adding zeros around the inputs.

In cases where the input image layer is to be connected to much smaller layer, technique to space out the receptive fields is implemented so that the model's computational complexity is dramatically reduced. This is new and special about the algorithm because it is not a generic method to implement stride. Since there is no guarantee what the input image would look like, an illustration for a 5×7 input layer (with zero padding) to connect to a 3×4 layer, using 3×3 receptive fields and a stride of 2 is illustrated in FIG. 17 Dimensionality Reduction. Here, the stride is the same in both directions, but it may not necessarily be so with the input images. A neuron located in row i, column j in the upper layer is connected to the outputs of the neurons in the previous layer located in rows i×$s_h$ to i×$s_h$+$f_h$-1, columns j×$s_w$ to j×$s_w$+$f_w$-1, where $s_h$ and $s_w$ are the vertical and horizontal strides.

Filters in Convolution Neural Network Layers (Steps 7, 8, 9):

A neuron's weights, which are referred to as filters or convolution kernels are assigned as a small image which is equal to the size of the receptive file. The first filter is a vertical filter which is a square matrix full of 0s except for the central $i^{th}$ column, of 1s); The corresponding neurons will ignore everything in their receptive field except for the central vertical line. This technique will ensure that the horizontal white lines get enhanced while the rest gets blurred. The second filter is a horizontal filter, which is again a square matrix full of 0s except for the central $j^{th}$ row, of 1s); The corresponding neurons using these weights will ignore everything in their receptive field except for the central horizontal line. This technique will ensure that the vertical white lines get enhanced while the rest gets blurred. During training the convolutional layer the algorithm will automatically learn the useful filters for its task of processing an image, and the layers described above will learn to combine them into more complex patterns. This allows this algorithm to stack such simple filters. Such combination of filters will be inputs in each convolution and the output is one feature map per filter. It has one neuron per pixel in each feature map, and all neurons within a given feature map share the same parameters. Neurons in different feature maps use different parameters. Thus, a convolutional layer simultaneously applies multiple trainable filters to its inputs, making it capable of detecting multiple features anywhere in its inputs. All neurons in a feature map share the same parameters, thus dramatically reducing the number of parameters in the model. Once the CNN has learned to recognize a pattern in one location of the image, it can recognize it in any other location within the image. Sometimes, in case of normal human leg photographs, images are composed of multiple sublayers: one per color channel. This case is illustrated in FIG. 18 Regular photograph with three colors. At a basic level, there are red, green, and blue (RGB) while grayscale images have just one channel. When some of the latest photography techniques are used, some images may also have extra light frequencies (such as infrared).

In this case, a neuron located in row i column j of the feature map k in a given convolutional layer l is connected to the outputs of the neurons in the previous layer l-1, located in rows i×$s_h$ to i×$s_h$+$f_h$-1 and columns j×$s_w$ to j×$s_w$+$f_w$-1, across all feature maps (in layer l-1).

In order to compute the output of a given neuron in a convolutional layer, the following formula is used:

$$z_{i,j,k} = b_k + \sum_{u=0}^{f_h-1} \sum_{v=0}^{f_w-1} \sum_{k'=0}^{f_{n'}-1} x_{i',j',k'} \times w_{u,v,k',k} \text{ with } \begin{cases} i' = ixs_h + u \\ j' = jxs_w + v \end{cases}$$

In this equation:
1. $z_{i,j,k}$ is the output of the neuron located in row i, column j in feature map k of the convolutional layer (layer l).
2. $s_h$ and $s_w$ are the vertical and horizontal strides, $f_h$ and $f_w$ are the height and width of the receptive field, and $f_{n'}$ is the number of feature maps in the previous layer (layer l-1).
3. $x_{i',j',k'}$ is the output of the neuron located in layer l-1, row i', column j', feature map k'.
4. $b_k$ tweaks the overall brightness of the feature map k (in layer l).
5. $w_{u,v,k',k}$ is the connection weight between any neuron in feature map k of the layer l and its input located at row u, column v and feature map k'.

Pooling Layers (Steps 7, 8.9 in Algorithm):

Pooling layers shrink the input image in order to reduce the computational load, the memory usage, and the number of parameters and this is specifically done to reduce the possibility of overfitting. Each neuron in a pooling layer is connected to the outputs of a limited number of neurons in the previous layer, located within a small rectangular receptive field. Its size, the stride, and the padding is defined, but the pooling neuron will be assigned no weights; all it does is aggregate the inputs using an aggregation function such as the max or mean. Only the max input value in each receptive field makes it to the next layer, while the other inputs are dropped. At the end of this step, the image still looks identical to the input image, but the pixel density is drastically reduced. This reduces the computations, memory usage, and the number of parameters. This stage will offer a small amount of rotational invariance and a slight scale invariance. This invariance is useful in cases where the prediction should not depend on these details for the classification task.

A few convolutional layers are stacked, and each one is followed by a rectified linear activation function or ReLU. This is a piecewise linear function to output the input directly if it is positive, otherwise, it will output zero. This ReLu is used to achieve better performance. The ReLU layer, then a pooling layer, then another few convolutional layers again followed by ReLU, then another pooling layer is part of this architecture. The input image gets smaller and smaller as it progresses through the network, but it also typically gets deeper with more feature maps. At the top of the stack, a regular feedforward neural network is added, with a few fully connected layers followed by ReLU and the final layer outputs the prediction.

FIG. 12 shows the convolutional blocks, with a depth of several layers, it is shown that a set of convolutions were followed by pooling. The input image is 300 by 300 pixels. There is a single neuron with a sigmoid activation on the output. The summary of the layers is also shown with the corresponding size changes. The first convolution reduces that to 147 by 147. From there, convolution loop repeats until its reduced to 35 by 35 which is then fed into the dense layers. A total of 40,165,409 trainable parameters were identified with this algorithm iteration.

While it is difficult to examine a CNN layer-by-layer, each layer's output can be visualized and extracted features seen. This is depicted in FIG. 13.

Softmax Classifier (Step 10 in Algorithm)

Refer to step 10 in the algorithm—the Softmax Regression classifier is used to predict only one class at a time. Even though it is generally used for multiclass since the outputs are strictly limited to mutually exclusive classes, this classification works inherently well for a clear, unequivocal classification. Overall the model is aimed at estimating probabilities and making predictions. The objective for the algorithm is to overall estimate a high probability 'p' for the intended class and consequentially a low probability '(1−p)' for the other class. This is accomplished by minimizing the cost function for cross entropy. The cross entropy is designed for measuring how well the estimated class probabilities matches the target class by penalizing the model when it estimates a low probability for a target class. The Cross entropy cost function is represented by the mathematical expression:

$$J(\theta) = -\frac{1}{m}\sum_{i=1}^{m}\sum_{k=1}^{K} y_k^{(i)} \log(\hat{p}_k^{(i)})$$

In this equation:

$y_k^{(i)}$ is the target probability that the $i^{th}$ instance belongs to class k. Since the prediction is either Yes or No, it will be a 1 or a 0 depending on whether the instance belongs to the class or not. If the assumptions are wrong, the cross entropy will be greater by an amount called the Kullback-Leibler (KL) divergence. The cross entropy in such cases, will be governed by $$H(p,q) = -\Sigma_x p(x) \log q(x)$$

where p and q represent the discrete probability distributions.

The gradient vector of this cost function with regard to $\theta^{(k)}$ is:

$$\nabla_{\theta^k} J(\theta) = \frac{1}{m}\sum_{1}^{m}((\hat{p}_k^{(i)} - y_k^{(i)})X^{(i)}$$

With this, the gradient vector for every class is computed and then Gradient Descent is used to find the parameter matrix Θ that minimizes the cost function determined by the cost entropy cost function.

Embodiment for Carrying Out the Invention

The invention is described below in detail with reference to the accompanying drawings.

FIG. 1 Overall system and Claims illustrates the overall system including LEG-Minder and LEGislator for the Leg Length discrepancy diagnosis system using Deep Neural Network (DNN) according to the present invention. The DNN section is explained in the section below:

Deep Neural Network Implementation

In order to non-linearly combine information in the server, Dense Neural networks is used. They are used in the server 'LEGislator' device. "LEGislator' can be used on its own to also make categorical predictions, although its primarily used to improve the CNN's accuracy in the LEG-Minder device (client). So, dense layers are on the server and they are hierarchically on top of the CNN architecture in the LEGMinder devices. This allows recombination of the information learned by the convolutional layers from the clients. This comprises of one passthrough input layer, one or more hidden layers, and the one final layer called the output layer. This is depicted in FIG. 18 Deep Neural Network. For this specification, the layers close to the input layer are referred to as the lower layers, and the ones close to the outputs are referred to as the upper layers.

The main components of the algorithm here are:

Algorithm in the server will handle one mini-batch at a time, and goes through the full training set multiple times. Each such pass is referred to in this specification as an Epoch.

Each mini-batch is passed to the network's input layer, which sends it to the first hidden layer.

The algorithm then computes the output of all the neurons in this layer for every Epoch.

The result is passed on to the next layer, its output is computed and passed to the next layer, and so on until it reaches the output layer. This is the forward pass: it is exactly like making predictions in the CNN, except all intermediate results are preserved.

Next, the algorithm measures the network's output error

Then it computes how much each output connection contributed to the error using chain rule.

The algorithm then measures how much of these error contributions came from each connection in the layer below all the way to the input layer. This will be done by propagating the error gradient backward through the network.

Next, Gradient Descent is performed to tweak all the connection weights in the network, using the error gradients just computed.

The Rectified Linear Unit function ReLU(z)=max(0, z) is used for this algorithm.

Referring to FIG. 1, the individual components comprise of a "LEGislator" based on ML which is connected to the Internet and performs DNN learning on the neural network of the "LEG-Minder" device. In particular, the present invention relates to a technology in which patient leg photos and diagnostic result data are acquired in each diagnosis center by the LEG-Minder device and then uploaded to the neural network learning server "LEGislator". The learning server performs DNN learning and updated the neural network model which in-turn is installed in the 'LEG-Minder' of the diagnosis center.

FIG. 2 is a block diagram of the LEG-Minder and the Neural Network Server "LEGislator" combination according to the present invention. This is a system level architecture representation showing the individual actions/functions that each of the devices would perform.

First, the component level architectures are described for easy understanding:

Component Level Description

Leg-Minder Device (100)

FIG. 3 Component Level architecture depicts the LEG-Minder Device (100). This device captures the input data from the patient and is equipped with neural network model which is preferably implemented as computer software or can be customized to a hardware.

The LEG-Minder device (100) captures the patient image either directly through a camera or allows uploading of the image (e,g., x-ray image) to the device using external means into the image processor module (110). In this specification, the neural network model which is initially installed in the LEG-Minder device (100) is referred to as the "current neural network model" (120). Further, in this specification, no-LLD refers to a photo/x-ray of a person that is classified NOT to have Anisomelia or Leg Length Discrepancy, whereas LLD represents one of a non-ignorable possibility of Leg Length Discrepancy and possibly requiring further examination by a specialist Orthopedic for treatment/rectification. The image is processed to find if the subject picture has LLD or Not by using the LLD Diagnosis module (130). When a new image is diagnosed by the LLD diagnosis module (130) the corresponding computation result, as to whether the subject image has LLD or not, is stored in the classified Diagnosis Database (140).

Periodically, the LEG-Minder device transfers it local Diagnosis Database (140) to the LEGislator though the Neural Network Updating module (150). The Neural Network updating module (150) also receives updated model from the LEGislator device (200), and updates the current neural network model (120). As the neural network updating module (150) updates the current neural network model (120), the version history is maintained in the "Version Control Module" (170).

There are two databases in the device, namely, the LLD database for storage of raw images (180), and a diagnosis database (140) consisting of images classified by the model.

Sentry Security module (160) ensure the integrity of the learned model as well as governs the security aspects related to sentry operations such as fending off any malicious attempts to induce bad data either at the network level or at the image ingress level for the LEG-Minder device (100).

Learning Server "LEGislator" (200):

FIG. 4 LEGislator Master Neural Network Server depicts the "LEGislator Device" (200). The function of the LEGislator Device is to perform transfer learning on the accumulated dataset, and to generate an upgraded neural network model to be disseminated to the LEG-Minder (100) device(s). The operations of LEGislator Device (200) is orchestrated by the Learning model orchestrator (210).

Upon initiation by the Learning model orchestrator (210), the LEG-Minder device(s) (100), will transfer their diagnosis database (140) to the Master LLD database (220). The transfer learning processor (240) then uses Deep Neural Network Model A (230) and the Master LLD database (220) to perform deep learning using DNN techniques to generate a Deep Neural Network Model B (250). Deep Neural Network Model B (250) is the embodiment of all the current learning in this client server architecture invention. The Server version tracker and distributor (280) keeps track of Deep Neural network model A (230) and the Deep Neural network model B (250). It performs a switch of model B to model A at the appropriate time as well as performs dissemination of the current model to all the LEG-Minder devices (100) via the Internet, thus performing an auto-upgrade. However, to prevent any spurious devices from getting updates or to ensure that no compromised LEG-Minder device (100) ever gets the update, the Server security module (260) ensures that proper Authentication, Authorization, Accounting and Auditing is conducted. For this purpose, Server security module (260) will work in conjunction with the Device version tracker (270). The Device version tracker (270) is a database that keeps track of every device that connects to the neural network, its associated credentials and security parameters to ensure integrity of the overall system.

After updating to the latest neural network model, the LEG-Minder updates its Version control (170). Depending on certain constraints, the Version control (170) may choose to accept or reject the downloaded version from the LEGislature device.

System Architecture:

At a system level the LEGislator and a plurality of the LEG-Minders form a client-server architecture, where in, the LEG-Minder is the client and the LEGislator is the server. This is depicted in FIG. 2 System Level Architecture.

Consider a healthcare network like that of Kaiser Permanente which is present in multiple locations and across multiple states within the USA. For example, Santa Clara, Fremont, Irvine, Atlanta etc. Each practice can cater to a certain number of patients. In the case of an orthopedic doctor, when the doctor sees a range of patients, they develop a certain level of knowledge. Given the regionalities, population density belonging to a certain ethic origin etc, they see a certain type of patients and they become experts within that population segment and 'know' what to expect. This based on the specialist's 'learning'. LA or Irvine might have a different set of patients who bring their own nuances. So, the "Legminder" is like a regional doctor. The plurality of the devices is referring to many such regional doctors who get their own regional learnings. They get their learning based on the patients they see.

In the above example, if we replace the regional doctors with one doctor who serves the entire humanity. Because he or she will see a vast number of patients, their knowledge base is HUGE. This is a direct relationship with the number of patients they see. So, the knowledge has a direct correlation with the "learning'. In this case, we have a server device, that takes the regional learnings and builds a master database, keeping track of the individual learnings (which is like a journal of regional doctors). In the case of the Kaiser Permanente scenario, we would rather see the entire network provide a similar experience to the patients. For this to happen in our case, we need every device working based on the same learning. Therefore server aggregates the learning, develops a common base from which each client needs to operate and serves this information to the individual client devices.

Since the 'LegMinder' is a machine, they need fool proof security measures. Hence the security aspects are embedded to prevent someone from providing pictures of donkey's legs versus the expected human legs for example.

As shown in FIG. 2, the Learning model orchestrator (210) controls the operations of the LEGislator 200. The Learning model orchestrator (210) performs four fundamental operations. Those are:

Initial Learning
Transfer Learning
Database Transfer, and
Upgrade

As shown in FIG. 2, the LEG-Minder 100 performs three fundamental operations. They are:
- Mission mode (Learn and Predict)
- Upgrade
- Transfer database Each of the operations mentioned above are described in greater detail in—FIG. 5, FIG. 6, FIG. 7, FIG. 8 and FIG. 9 each process step described in detail as below:

Step A Initial Learning

As shown in FIG. 5, upon receiving the trigger from the learning model orchestrator (210), the Transfer learning processor (240) will perform:

STEP A1: Initiate learning sequence with its associated image generators and create train and validation datasets as described in the Algorithm Summary.

STEP A2: Generate CNN model by stacking multiple sets of convolutions and pooling layers along with the dense layers, and a SoftMax classifier STEP A3: Adjust model fit by adjustable parameters such as the learning rate STEP A4: Save the resulting Neural network model "B" in the server version tracker and distributor (280).

Step B Upgrade LEG Minder

As outlined in FIG. 6 Step B Upgrade LEG Minder, the output of STEP A above is used to update the LEG-Minder (100) device. Steps associated with this areas described below with reference to FIG. 6:

STEP B0: The LEGislator device (200) will, upon initiation from the learning model orchestrator (210) initiate the upgrade command to LEG-Minder device(s) (100).

STEP B1: The upgrade process is initiated by the Server version tracker and distributor (280) over an Internet connection.

STEP B2: The LEG-Minder device (100) receives the command into the Sentry Security module and authenticates the command received.

STEP B3: Upon authentication, the Neural network updating module (150) will update the current neural network model sent by the LEGislator device (200).

STEP B4: Upon successful update verification by Neural network updating module (150), the version control module (170) will update the version number.

STEP B5: The current neural network model (120) is then replaced with the newly downloaded model.

Step C Transfer Data

At this point the LEG-Minder device has acquired all the new learnings from the server and continues to diagnose LLD and update its database as described in the component section. To provide the new learnings back to the LEGislator server the following steps are used as shown in FIG. 7:

STEP C0: A transfer command is issued by the learning model orchestrator (210) of the LEGislator device (200)

STEP C1: A command is issued to initiate the transfer process by the Server version tracker and distributor (280) over an Internet connection to specific LEG-Minder device (100).

STEP C2: The Sentry Security module (160) receives it, authenticates that it is intended for the correct LEG-Minder device (100) and then relays it to the Neural Network Updating module (150).

STEP C3: The Neural Network Updating module (150) initiates upload of the diagnosis database (140) to the LEGislator (200) via the Internet STEP C4: The Server security module (260) ensures that proper Authentication, Authorization, Accounting and Auditing and relays command to the Server version tracker and distributor (280).

STEP C5: The Server version tracker and distributor (280) then saves the uploaded images to the Master LLD database (220).

This will initiate the transfer learning process in the LEGislator (200) as shown in FIG. 8.

Step D Transfer Learning

As shown in FIG. 8, STEP D0: A transfer learning command is issued by the learning model orchestrator (210) of the LEGislator device (200)

STEP D1: The transfer learning processor (240) then uses Deep Neural Network Model A (230) and the Master LLD database (220) to perform deep learning using DNN techniques.

STEP D2: Above step results in generation of the Deep Neural Network Model B (250).

STEP D3: The updated network model is saved in Device version tracker (270) along with the credentials of the LEG-Minder (100) and the Server version tracker and distributor (280).

Step E Mission Mode

When the LEG-Minder Device (100) is in Mission mode as shown in FIG. 9, it is ready of diagnosis. When a new image is presented to the LEG-Minder Device (100) for diagnosis of LLD, it performs the following steps:

STEP E1: The image processor (110) processes the image per the algorithm described under Algorithm Summary:

STEP E2: Using the current neural network model (120) and the LLD Diagnosis module (130) to process the image, make a prediction and then update the Diagnosis database (140) and the LLD database (180).

Technology Definitions

The "Deep Learning" technology refers to a technology by which computers may think and learn like a human, especially to group or categorize objects and data. Deep-learning methods are representation-learning methods with multiple levels of representation, obtained by composing simple but non-linear modules that each transform the representation at one level into a representation at a higher, slightly more abstract level. The key aspect of deep learning is that these layers of features are not designed by human engineers: they are learned from data using a general-purpose learning procedure as used in this invention.

The deep learning is a machine learning technique which is proposed for overcoming the limitation of "Artificial neural network" algorithm. The Deep learning has two kinds of data categorization approach, i.e., supervised learning and unsupervised learning. In the supervised learning approach, a computer is trained with well-categorized information. This invention uses supervised learning.

Deep learning in this invention uses a pipeline of modules all of which are trainable. This allows for multiple stages in the process of recognizing an object and all of those stages are part of the training for subsequent model generations i.e., representations are hierarchical and trained.

The invention claimed is:

1. A computerized method,
  which is implementable by using at least: one or more hardware processors that are configured to execute code, and that are operably associated with one or more memory units that are configured to store code;

wherein the computerized method comprises:

determining whether a particular subject has a Leg Length Discrepancy (LLD), by performing:

(a1) receiving a training set of images of legs of patients;

(a2) receiving a validation set of images of legs of patients;

(b) operating on the training set of images by:

(b1) performing image normalization and image resizing on said images of legs of patients;

(b2) modifying the images of the training set, by applying one or more image transformation operations selected from the group consisting of: image rotation, image flip, skewing, zoom modification, isotropic scaling, shear transformation;

(b3) performing a binary-type classification of said images of legs of patients, into exactly one of: (i) a first class of images that includes only images that are determined to not be associated with LLD, or (ii) a second class of images that includes both images that are determined to be associated with LLD and images that are determined to possibly be associated with LLD;

(b4) passing the images of the training set of images via convolutions and extracting a first set of unique features from said images of the training set; and operating a Convolutional Neural Network (CNN) unit which applies convolution, kernel initialization, pooling, activation, padding, batch normalization, and stride to the images, to detect one or more particular image-features that are determined to be predictive for LLD detection;

(b5) perform pooling and image traversal, through a particular path of convolutions that was passed in step (b4), and concurrently extracting a next set of unique features from said images of the training set by using computerized-vision object detection and computerized-vision pattern recognition;

(b6) stacking multiple sets of convolutions that were passed in step (b4), and also stacking multiple pooling layers that were pooled in step (b5), to generate reduced-size images;

(b7) feeding the reduced-size images into one or more dense layers of said CNN unit;

(b8) applying a SoftMax classifier to reduce binary loss, and further applying a sigmoid classifier;

(b9) adjusting a learning rate of said CNN unit for convergence into a solution;

(b10) generating by said CNN unit a single-neuron output with a sigmoid activation, which indicates a binary-type output with regard to a particular image; wherein the binary-type output is either (i) the particular image is not associated with LLD, or (ii) the particular image is associated or is possibly associated with LLD;

(c) operating on the validation set of images by:

performing steps (b1) through (b10) on the validation set of images to verify an accuracy of classifications performed by said CNN unit.

2. The computerized method of claim 1, wherein said images of legs of patients include both (i) X-Ray images of legs of patients and (ii) photographic non-X-Ray images of legs of patients.

3. The computerized method of claim 1, wherein said images of legs of patients include, exclusively, X-Ray images of legs of patients.

4. The computerized method of claim 1, wherein said images of legs of patients include, exclusively, photographic non-X-Ray images of legs of patients.

5. The computerized method of claim 1, further comprising:

collecting said images of legs of patients at a central server, from a plurality of remote imaging devices that are located at a plurality of remote locations;

generating a unified Deep Neural Network (DNN) model based on said images of legs of patients that were collected from said plurality of remote imaging devices that are located at said plurality of remote locations;

wherein the DNN model is configured to reduce bias or to eliminate bias in diagnosis of LDD by performing training and convolutions on said images of legs of patients that were collected from said plurality of remote imaging devices that are located at said plurality of remote locations, rather than by relying on legs images from a single source or from a single hospital or from a single locality.

6. The computerized method of claim 5, further comprising:

operating a security module that secures an integrity of said unified Deep Neural Network (DNN) model from malicious attacks, and that blocks malicious attacks to introduce bad data (i) at said central server at a network level, and (ii) at said plurality of imaging devices at an image ingress level.

7. The computerized method of claim 6, further comprising:

performing a transfer learning process at said central server, on a dynamically-updated dataset of images of legs of patients; periodically generating at said central server an upgraded DNN model; and periodically sending the upgraded DNN model to the plurality of imaging devices.

8. The computerized method of claim 6, wherein said DNN model is configured to detect LLD of a particular person, based on a group photograph that depicts two or more persons standing together.

9. The computerized method of claim 1, wherein said images of legs of patients include, exclusively, side images of legs of patients, and not frontal images of legs of patients.

10. The computerized method of claim 1, wherein said images of legs of patients include both: (i) side images of legs of patients, and (ii) frontal images of legs of patients.

11. The computerized method of claim 1, wherein the CNN model is developed and is dynamically updated at a central server computer based on images of legs that are uploaded to said central computer server from a plurality of end-user devices;

wherein a current version of the CNN model is periodically distributed from said central server computer to said end-user devices, and dynamically replaces on said end-user devices a prior version of the CNN model;

wherein central upgrading of the CNN model, based on images of legs that are uploaded to said central computer server from a plurality of end-user devices that are located at a plurality of different locations, causes the CNN model and the determining of LLD to be more resilient to bias.

12. A computerized system, which is implemented by utilizing at least: one or more processors that are configured to execute code, and that are operably associated with one or more memory units that are configured to execute code;

wherein the system comprises:

(a) a plurality of distributed end-user devices, wherein each end-user device is an electronic device selected from the group consisting of: a smartphone, a tablet, an electronic device comprising a processor and an imager;

wherein each end-user device is configured to acquire digital non-radiological non-X-Ray photographs of legs of persons;

wherein each end-user device is configured to perform: (i) a learn-and-predict process, (ii) a Deep Neural Network (DNN) model upgrade process, and (iii) a database transfer process;

wherein each end-user device locally-stores therein, and locally-runs therein, a local version of a DNN model that is periodically updated by a central computer server;

(b) said central computer server, that is configured to communicate separately, over Internet-based communication links, with each one of the plurality of distributed end-user devices;

wherein the central computer server comprises a DNN Engine, that is configured to perform: (i) an initial learning process, (ii) a transfer learning process, (iii) a further database transfer process, and (iv) a further DNN model upgrade process;

wherein the DNN Engine periodically upgrades the DNN model, and periodically distributes an upgraded DNN model to each one of said end-user devices;

wherein at least one of: (I) the plurality of end user devices, (II) said central computer server, is configured to utilize said upgraded DNN model to generate a determination for diagnosis, indicating whether or not a particular subject has a Leg Length Discrepancy (LLD), by feeding a digital non-radiological non-X-Ray photograph of legs of said particular subject into said upgraded DNN model, based on output from a sigmoid-activated single-neuron of said DNN model;

wherein an accuracy of the diagnosis of LLD, by each of the plurality of end-user devices, or the said central computer server, gradually improves based on cumulative DNN learning by the central computer server which is based on analysis of images from the plurality of end-user devices.

13. The computerized system of claim 12, wherein the central server computer stores at least: (i) a first version of the DNN model, which is currently being utilized for LLD determination by at least one end-user device; and also, (ii) a second version of the DNN model, which is an upgraded version of the DNN model that is more accurate than the first version of the DNN model, and which is pending for distribution to one or more end-user devices.

14. The computerized system of claim 12, wherein each end-user device periodically replaces, a current-version of the DNN model that is stored locally and is utilized locally in the end-user device, with an upgraded-version of the DNN model that is periodically received over an Internet-based communication link from said central computer server.

15. The computerized system of claim 12, wherein each end-user device is equipped with a security module that is configured to block malicious images from being added to a locally-stored dataset of images and from being copied upstream to said central computer server.

16. The computerized system of claim 12, wherein the central computer server comprises:

a Master LLD Database which stores images that are utilized by the central computer server to generate and to update the DNN model for detection of LLD; and a Transferred Learning LLD Database which stores images that were received from a particular end-user device and that were not yet utilized for updating the DNN model;

wherein a DNN Model Updater Unit operates to upgrade or improve the DNN model based on the images in the Transferred Learning LLD Database; and wherein content of the Transferred Learning LLD Database is then added to the Master LLD Database of the central computer server.

17. The computerized system of claim 12, wherein said DNN model is configured to detect LLD of a particular person, based on a group photograph that depicts two or more persons standing together.

18. The computerized system of claim 12, wherein said images of legs of patients include, exclusively, side images of legs of patients, and not frontal images of legs of patients.

19. The computerized system of claim 12, wherein said images of legs of patients include both: (i) side images of legs of patients, and (ii) frontal images of legs of patients.

20. The computerized system of claim 12, wherein the CNN model is developed and is dynamically updated at the central server computer based on images of legs that are uploaded to said central computer server from said plurality of end-user devices;

wherein a current version of the CNN model is periodically distributed from said central server computer to said end-user devices, and dynamically replaces on said end-user devices a prior version of the CNN model;

wherein central updating of the CNN model, based on images of legs that are uploaded to said central computer server from a plurality of end-user devices that are located at a plurality of different locations, causes the CNN model and the determining of LLD to be more resilient to bias.

* * * * *